United States Patent [19]

Pannek, Jr.

[11] Patent Number: 5,224,945
[45] Date of Patent: Jul. 6, 1993

[54] COMPRESSIBLE/EXPANDABLE ATHERECTOMY CUTTER

[75] Inventor: Edward J. Pannek, Jr., Oceanside, Calif.

[73] Assignee: InterVentional Technologies, Inc., San Diego, Calif.

[21] Appl. No.: 820,089

[22] Filed: Jan. 13, 1992

[51] Int. Cl.5 .......................................... A61B 17/32
[52] U.S. Cl. .................... 606/159; 606/170; 606/180; 604/22
[58] Field of Search .................. 604/22; 606/155, 170, 606/180, 191, 194; 15/104.19; 128/751-754

[56] References Cited

U.S. PATENT DOCUMENTS

| | | | |
|---|---|---|---|
| 2,556,783 | 6/1951 | Wallace | 128/321 |
| 2,729,210 | 1/1956 | Spencer | 128/2 |
| 2,730,101 | 1/1956 | Hoffman | 128/305 |
| 2,749,909 | 6/1956 | Ullery et al. | 128/2 |
| 3,320,957 | 5/1967 | Sokolik | 128/311 |
| 3,512,519 | 10/1967 | Hall | 128/2 |
| 3,605,721 | 9/1971 | Hallac | 128/2 B |
| 3,815,604 | 6/1974 | O'Malley et al. | 128/305 |
| 3,990,453 | 11/1976 | Doaves et al. | 128/305 |
| 4,112,207 | 8/1978 | Seiler, Jr. | 128/305 |
| 4,273,128 | 6/1981 | Lary | 128/305 |
| 4,320,762 | 3/1982 | Bentov | 128/343 |
| 4,415,509 | 4/1984 | Kotsifas et al. | 128/757 |
| 4,445,509 | 5/1984 | Auth | 128/305 |
| 4,589,412 | 5/1986 | Kensey | 128/305 |
| 4,598,710 | 7/1986 | Kleinberg | 128/318 |
| 4,603,694 | 8/1986 | Wheeler | 128/312 |
| 4,610,662 | 9/1986 | Weikl et al. | 604/53 |
| 4,627,436 | 12/1986 | Leckrone | 128/303.1 |
| 4,631,052 | 12/1986 | Kensey | 604/22 |
| 4,636,195 | 1/1987 | Wolinsky | 604/53 |
| 4,640,296 | 2/1987 | Schnepp-Pesch et al. | 128/754 |
| 4,646,738 | 3/1987 | Trott | 128/305 |
| 4,650,466 | 3/1987 | Luther | 604/95 |
| 4,653,496 | 3/1987 | Bundy et al. | 128/305 |
| 4,655,217 | 4/1987 | Reed | 128/305 |
| 4,655,771 | 4/1987 | Wallsten | 623/1 |
| 4,664,112 | 5/1987 | Kensey et al. | 128/341 |
| 4,665,918 | 5/1987 | Garza et al. | 128/343 |
| 4,669,469 | 6/1987 | Gifford, III et al. | 128/305 |

(List continued on next page.)

FOREIGN PATENT DOCUMENTS

| | | | |
|---|---|---|---|
| 0117519 | 2/1984 | European Pat. Off. | 606/159 |
| 3732236 | 12/1988 | Fed. Rep. of Germany | 606/159 |
| 0002523 | 3/1990 | World Int. Prop. O. | 606/159 |

OTHER PUBLICATIONS

Banning G. Lary, M. D., Method for Increasing the Diameter of Long Segments of the coronary Artery, *The American Surgeon*, Jan., 1966. vol. 32. No. 1, pp. 33-35.

Banning G. Lary, M. D., and Roger W. Sherman, M. D., A Method for Creating a Coronary-Myocardial Artery, *Surgery*, St. Louis, Jun. 1966. vol. 59. No. 6, pp. 1061-1064.

Banning G. Lary, M. D., Coronary Artery Incision and Dilation, *Archives of Surgery*, Dec. 1980. vol. 115. pp. 1478-1480.

Primary Examiner—C. Fred Rosenbaum
Assistant Examiner—William H. Lewis
Attorney, Agent, or Firm—Nydegger & Associates

[57] ABSTRACT

An expandable and compressible atherectomy cutter for cutting plaque from a stenosis in an artery includes a cutter assembly which, relative to its axis of rotation, has a plurality of radially separated and axially aligned blades. The distal ends of these blades are joined together at a grommet and the proximal ends are free for individual engagement with grooves which are axially oriented on the hub of a rotatable torque tube. Each groove on the hub has a plurality of notches, and each notch in a groove has a corresponding notch in each of the other grooves which lies in the same radial plane and at the same radial distance from the rotational axis of the torque tube. Although notches in different radial planes can have different radial distances, the proximal ends of the blades simultaneously engage with only the notches in the same radial plane. Thus, movement of the cutter assembly relative to the hub causes a concerted movement of the proximal ends of the blades from notches in one radial plane to the notches in another radial plane for radial expansion or contraction of the blades.

16 Claims, 5 Drawing Sheets

U.S. PATENT DOCUMENTS

| | | | |
|---|---|---|---|
| 4,679,557 | 7/1987 | Opie et al. | 128/305 |
| 4,685,458 | 8/1987 | Leckrone | 128/303 |
| 4,686,982 | 8/1987 | Nash | 128/305 |
| 4,690,140 | 9/1987 | Mecca | 128/305 |
| 4,696,667 | 9/1987 | Masch | 604/22 |
| 4,706,671 | 11/1987 | Weinrib | 128/348.1 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,756,332 | 8/1988 | Fischell et al. | 128/305 |
| 4,757,826 | 7/1988 | Abdulhay | 128/757 |
| 4,857,045 | 8/1989 | Rydell | 604/22 |
| 4,886,061 | 12/1989 | Fischell et al. | 604/22 |
| 4,887,613 | 12/1989 | Farr et al. | 606/159 |
| 4,895,166 | 1/1990 | Farr et al. | 128/751 |
| 4,895,560 | 1/1990 | Papantonakos | 606/159 |
| 4,950,277 | 8/1990 | Farr | 606/159 |
| 4,966,604 | 10/1990 | Reiss | 606/159 |
| 4,986,807 | 1/1991 | Farr | 604/22 |
| 5,019,088 | 5/1991 | Farr | 606/159 |
| 5,030,201 | 7/1991 | Palestrant | 604/22 |
| 5,071,424 | 12/1991 | Reger | 606/170 |
| 5,100,425 | 3/1992 | Fischell et al. | 606/159 |

COMPRESSIBLE/EXPANDABLE ATHERECTOMY CUTTER

FIELD OF THE INVENTION

The present invention pertains generally to medical devices which are useful for removing a stenotic segment from the artery of a patient. More particularly, the present invention pertains to atherectomy devices which cut plaque from an artery. The present invention is particularly, but not exclusively, useful as an atherectomy cutter which has expandable/compressible blades for varying the cutting radius of the device.

BACKGROUND OF THE INVENTION

It is well known that any significant reduction or restriction in the flow of blood through the arteries of the body can cause complications which may have serious consequences. In any event, it is extremely important for the health of the patient that a stenosis, or blockage, which is causing such a condition be eliminated. One well known and frequently used procedure to accomplish this task is popularly known as angioplasty. For a basic angioplasty procedure, a dilatation balloon is positioned in the arterial lumen at the stenosis and the balloon is inflated to open the artery by dilating the plaque-restricted lumen at the stenosis. The plaque, however, remains in the artery and is not removed. Unfortunately, in some cases, it appears that the plaque which is left behind in the artery may cause another stenosis to form.

As an alternative to angioplasty, atherectomy procedures have been developed to resolve the problems caused by blocked arteries. However, unlike an angioplasty procedure which only dilates the lumen at the stenosis but does not remove the plaque from the artery which caused the stenosis, in accordance with an atherectomy procedure the plaque which is creating the stenosis is mechanically cut from the artery and then removed. The cutting devices which are used for this task must, of necessity, be rather small. On the other hand they must have sufficient structural strength to cut the plaque in performance of the atherectomy procedure. Additionally, they must be operationally reliable. Many examples of such cutting devices can be given. For instance, U.S. Pat. No. 4,895,166 which issued to Farr et al. for an invention entitled "Rotatable Cutter for the Lumen of a Blood Vessel", and which is assigned to the same assignee as the present invention, discloses such a cutter. U.S. Pat. No. 4,589,412 which issued to Kensey for an invention entitled "Method and Apparatus for Surgically Removing Remote Deposits" is but another example.

One problem which must be confronted in any procedure, whether it be an angioplasty or an atherectomy procedure, is the size of the entry site which can be used for introducing the medical device being used into the artery. Standard practices accept an entry site which has a diameter of only approximately twelve French, i.e. about four millimeters. Thus, any device which is to be positioned in the artery must pass through an introducer whose outer diameter is not larger than twelve French. The inner diameter of such an introducer is generally, however, on the order of only nine French. The consequence is that any device which is effectively insertable into the artery of a patient must be capable of assuming a configuration wherein the greatest dimension across the device is no more than approximately seven French. It happens, however, that to properly clear a stenotic segment it is sometimes necessary to create a lumen which has a greater diameter than seven French. To do this by an atherectomy procedure, the cutter being used must be capable of expanding beyond the seven French restriction imposed at the entry site.

Several examples of expandable cutting devices which are specifically useful as medical devices for atherectomy procedures can be given. U.S. Pat. No. 4,966,604 which issued to Reiss for an invention entitled "Expandable Atherectomy Cutter with Flexibly Bowed Blades", and U.S. Pat. No. 4,986,807 which issued to Farr for an invention entitled "Atherectomy Cutter with Radially Projecting Blade", both of which patents are assigned to the same assignee as the present invention, pertain to expandable atherectomy cutters. There is, of course, still a need for other expandable atherectomy cutters which can meet the specific needs of a specifically desired protocol.

The present invention recognizes that several factors need to be considered when determining the most desirable structure for an expandable atherectomy cutter and its method of use. First, there is the need to satisfy the personal preferences of the particular surgeon who is to perform the atherectomy operation. Clearly, different surgeons can have different approaches to the solution of the same problem. Further, there is the need to provide a structure which is best suited for performance of the particular task. It happens that atherectomy procedures can be performed in the coronary arteries, the carotid arteries, the renal arteries, and in the peripheral arteries. Each set of arteries is different and presents different challenges to the atherectomy procedure. The present invention provides such a structure for consideration and use by the operating physician.

In light of the above it is an object of the present invention to provide a compressible/expandable atherectomy cutter which can be reconfigured within an artery by manipulations performed externally of the patient. Another object of the present invention is to provide a compressible/expandable atherectomy cutter which can be configured into an operational rigid cutting configuration. Still another object of the present invention is to provide a compressible/expandable atherectomy cutter which is capable of making a reliable transition between a compressed configuration and an expanded configuration. Yet another object of the present invention is to provide a compressible/expandable atherectomy cutter which expands into a structurally predictable configuration. Another object of the present invention is to provide a compressible/expandable atherectomy cutter with is relatively simple to use, relatively easy to manufacture, and comparatively cost effective.

SUMMARY OF THE INVENTION

For the present invention, an expandable and compressible atherectomy cutter includes a guide wire which is formed with an abutment. The guide wire is slidingly insertable through a rotatable torque tube and through a hub which is mounted at the distal end of the tube. The cutter also includes at least one blade which has a distal end that is slidingly engaged with the guide wire, and which has a proximal end that is slidingly mounted on the hub. The hub itself is formed with a corresponding groove for each blade, and each groove on the hub is substantially aligned with the axis of rotation of the cutter. A plurality of notches are formed along the bottom of each groove, and each notch in a groove has a corresponding notch in each of the other grooves which lies in the same radial plane. Further, all notches in the same radial plane are located at essentially the same radial distance from the axis of rotation of the cutter. In the preferred embodiment of the present invention, each groove has a proximal notch, a distal notch, and an intermediate notch therebetween, which respectively lie in the same radial plane with all of the other corresponding proximal, distal or intermediate notches. Additionally, the radial distance for each of the proximal and distal notches is less than the radial distance for the intermediate notches.

As intended for the present invention, the distal ends of each of the blades are joined together and held by a grommet which is slidingly positioned over the guide wire. On the other hand, the proximal end of each blade is slidingly mounted on the hub. As so mounted the proximal end of blade is positioned to lie in the same radial plane with the proximal ends of the other blades. Thus, all proximal ends simultaneously engage with either the proximal notches, the intermediate notches, or the distal notches. When the proximal ends of the blades are engaged with either the proximal or the distal notches in the grooves on the hub, the blades are held in a compressed configuration which has a reduced cutting radius. When these same ends are engaged with the intermediate notches, the blades are held in an expanded configuration wherein the blades are spread outwardly to have an increased cutting radius. In accordance with the present invention, the cutter is placed in a compressed configuration for insertion of the cutter through an introducer tube into the artery. Once in the artery, the cutter is manipulated into its expanded configuration for cutting plaque from the stenotic segment. Subsequently, after the plaque has been cut and removed from the stenotic segment, the cutter is again placed in its compressed configuration for withdrawal and removal of the cutter from the artery.

Movement of the cutter from the compressed configuration to the expanded configuration, and back to the compressed configuration, is accomplished by urging the abutment on the guide wire against the grommet which holds the distal ends of the blades together. As indicated above, these changes in configuration are accomplished for procedural purposes. Initially, the cutter is in a compressed configuration with the proximal ends of the blades engaged in the proximal notches on the hub. With this configuration the cutter is introduced into the artery. The cutter is then expanded to cut plaque from the stenotic segment in the artery. To do this, the abutment which is located distally from the grommet is pulled proximally to urge the abutment against the grommet. This moves the cutter into its expanded configuration wherein the proximal ends of the blades are engaged with the intermediate notches. After the plaque has been cut from the stenotic segment, further proximal movement of the abutment against the grommet moves the cutter into its compressed configuration with the proximal end of the blades engaged with the proximal notches on the hub. The cutter can then be withdrawn from the artery.

In an alternate embodiment of the present invention, the initial compressed configuration is assumed with the proximal ends of the blades located in the distal notches in the grooves of the hub. The abutment is located distally from the grommet and the changes in configuration are accomplished by pulling proximally on the guide wire to urge the abutment against the grommet and move the proximal ends of the blades sequentially from the distal notches, to the intermediate notches, and finally to the proximal notches.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
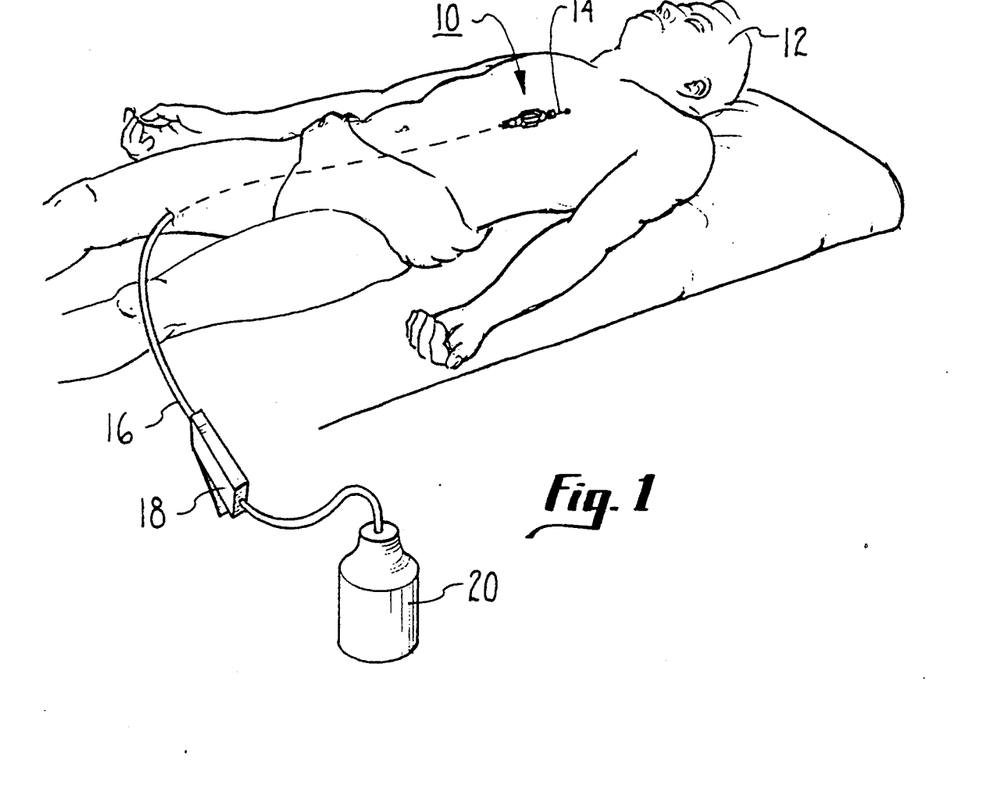
FIG. 1 is a perspective view of an operational atherectomy system using the expandable/compressible cutter of the present invention.

An expandable/compressible atherectomy cutter in accordance with the present invention is shown in FIG. 1 in its operational environment and is generally designated 10. As shown, the cutter 10 has been inserted into an artery of the patient 12 and positioned in the artery for the purpose of removing plaque from a stenosis in the artery. In order to properly position the cutter 10 in the artery, it is inserted over a previously positioned guide wire 14. Once the cutter 10 is properly positioned against a stenotic segment in an artery of the patient 12, the cutter 10 is rotated by the rotatable torque tube 16 to cut plaque from the stenosis. This is controlled by the control unit 18. Additionally, control unit 18 also controls the operation of a vacuum source 20 which creates suction through the torque tube 16 to remove cut plaque from the artery of the patient.

Figure 2:
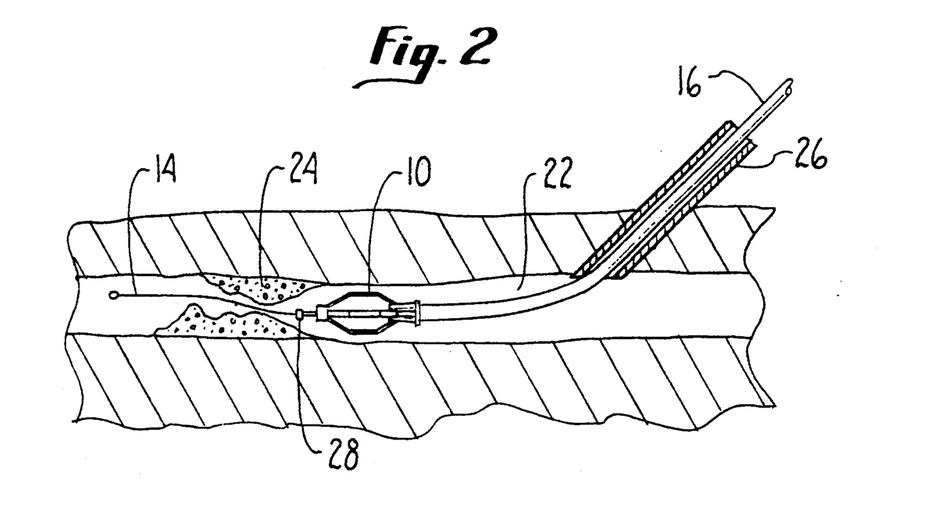
FIG. 2 is a cross-sectional view of an artery in a patient having a stenotic segment in the artery with the cutter of the present invention operationally positioned in the artery.

The actual operational environment for the cutter 10 is, perhaps, best appreciated with reference to FIG. 2. There it will be seen that the cutter 10 is positioned in an artery 22 against the plaque 24 of a stenosis in the artery 22. Importantly, the cutter 10 has been inserted into the artery 22 through an introducer catheter 26. As indicated above, the introducer catheter 26 is limited by conventional protocols as to how large its outside diameter can be. Typically, introducer catheters 26 have outside diameters that are approximately twelve French (one French is approximately equal to one third millimeter). The consequence is that the inside diameter of introducer catheter 26 is on the order of only nine French. Thus, cutter 10 must be compressible to a configuration having a dimension less than nine French which can be inserted through introducer catheter 26. The structure used for cutter 10 to accomplish this is best seen in FIG. 3.

Figure 3:
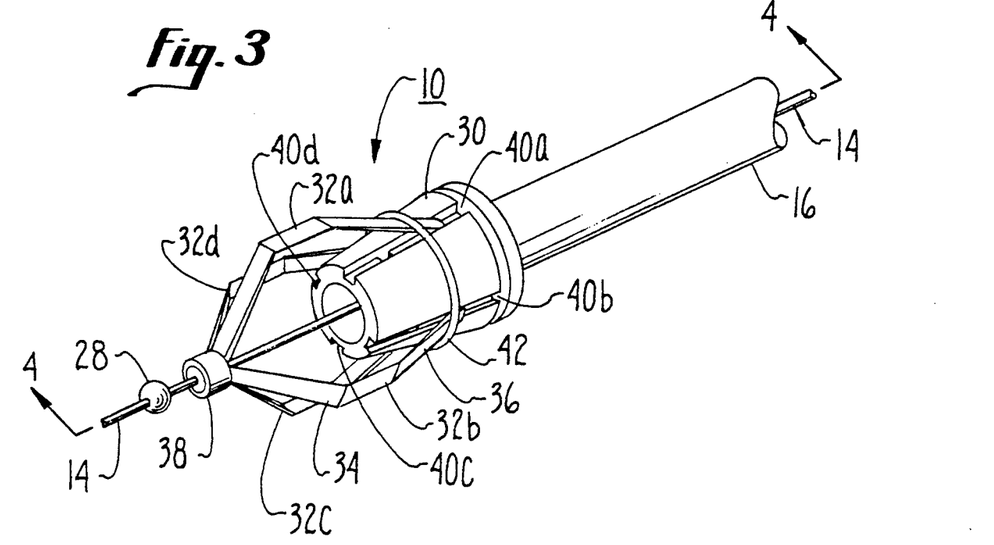
FIG. 3 is a perspective view of an embodiment of the expandable/compressible cutter of the present invention.

FIG. 3 shows that the flexible guide wire 14 has an abutment 28 which is located distally from the cutter 10. FIG. 3 also shows that a hub 30 is fixedly attached to the distal end of torque tube 16 for rotation by the tube 16. Further, the cutter 10 is shown to include a plurality of blades 32 $a,b,c,d$. More specifically, each blade 32 $a,b,c,d$ has a distal end 34 and a proximal end 36, and the distal end 34 of each blade 32 is attached to a grommet 38 which is slidingly disposed over the guide wire 14. The proximal end 36 of each blade 32 $a,b,c,d$ is slidingly engaged with a respective groove 40 $a,b,c,d$ which is formed on the hub 30 and is held in this sliding engagement against the hub 30 by the action of a spring means, such as an elastic band 42.

Figure 4A:
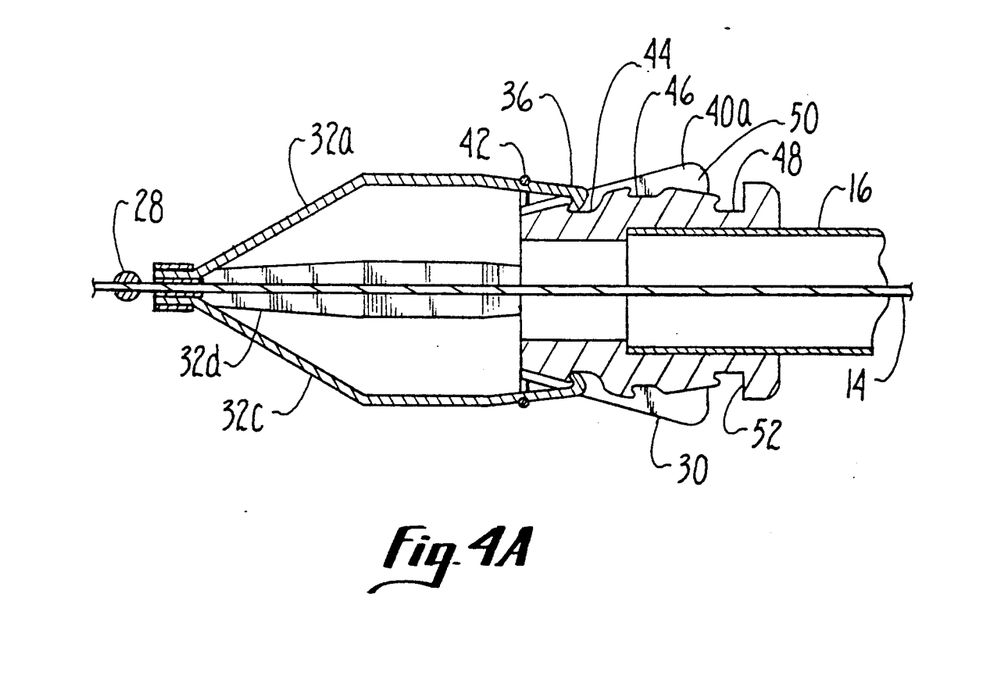
FIG. 4A is a cross-sectional view of the embodiment of the cutter of the present invention in a compressed entry configuration as seen along the line 4—4 in FIG. 3.

The interaction between the proximal ends 36 of blades 32 $a,b,c,d$ and hub 30 will be best seen with reference to FIG. 4A. From FIG. 4A it will be appreciated that the bottom of each groove 40 $a,b,c,d$ is formed with a distal notch 44, an intermediate notch 46 and a proximal notch 48. Importantly, these notches 44, 46 and 48 have specific geometric relationships with respect to each other. In order to describe these relationships, consider cutter 10 to have an axis of rotation that lies generally along a line that is coincident with the guide wire 14 as shown in FIG. 4A. Using this axis of rotation as a reference, each distal notch 44 lies in the same radial plane with the distal notches 44 in the other grooves 40. Likewise, all intermediate notches 46 lie in the same radial plane and all proximal notches 48 lie in their same radial plane. Further, the radial distance of each distal notch 44 from the axis of rotation is the same as for every other distal notch 44 and the same is true for the radial distances of the intermediate notches 46 and the proximal notches 48. It happens, however, that the radial distances of the intermediate notches 46 from the axis of rotation are greater than the radial distances of either the distal notches 44 or the proximal notches 48. Preferably, the radial distances of the distal notches 44 and the proximal notches 48 are approximately the same. FIG. 4A also shows that the sides 50 of a groove 40 contain the proximal end 36 of each blade 32 $a,b,c,d$ within the groove 40. Consequently, the blades 32 $a,b,c,d$ will rotate with hub 30 upon rotation of the torque tube 16.

Figure 4B:
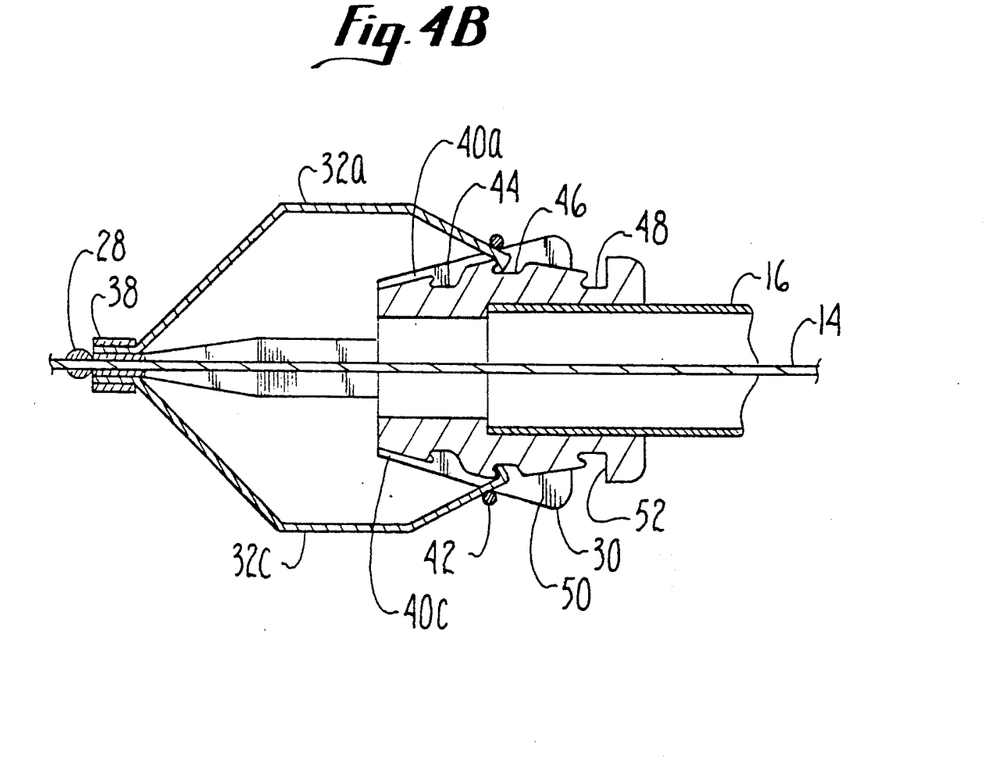
FIG. 4B is a cross-sectional view of the embodiment of the cutter of the present invention as seen in FIG. 4A with the cutter in an expanded configuration.
Figure 4C:
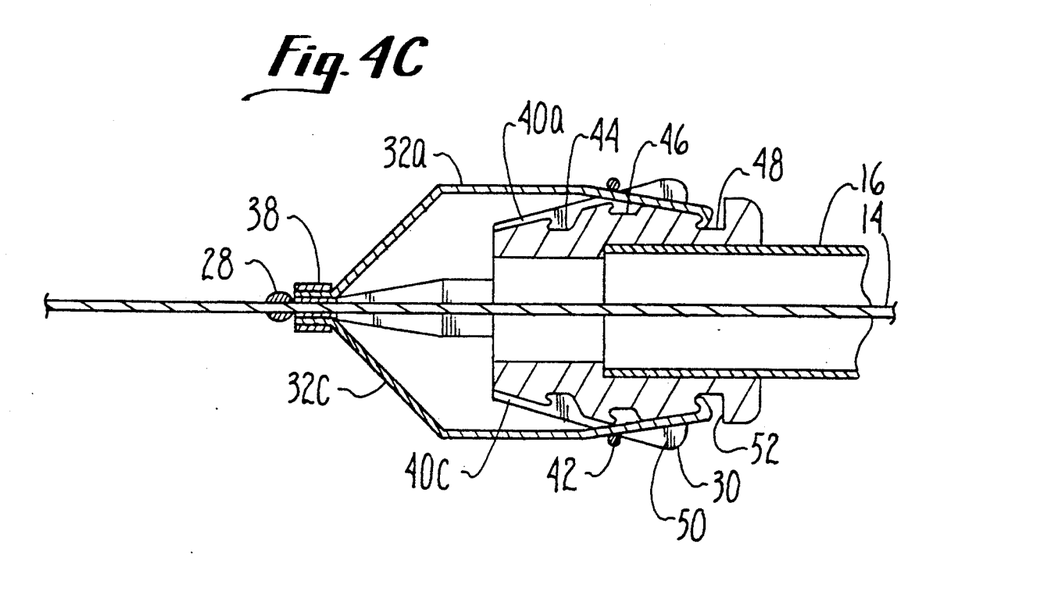
FIG. 4C is a cross-sectional view of the embodiment of the cutter of the present invention as seen in FIG. 4A with the cutter in a compressed withdrawal configuration.

The operation of cutter 10 will be best appreciated by cross referencing FIGS. 4A, 4B and 4C. Both FIG. 4A and 4C show the cutter 10 in its compressed configuration while FIG. 4B shown the cutter 10 in its expanded configuration. Specifically, FIG. 4A shows cutter 10 with the proximal ends 36 of blades 32 $a,b,c,d$ engaged with the distal notches 44 in grooves 40 of hub 30. This establishes cutter 10 with a dimensional configuration which allows the cutter 10 to be inserted into artery 22 through the introducer catheter 26.

Manipulation of the cutter 10 from its compressed configuration (shown in FIG. 4A) into its expanded configuration (shown in FIG. 4B) is accomplished by pulling proximally on the guide wire 14. This action brings the abutment 28 into contact with the grommet 38 and simultaneously urges all blades 32 $a,b,c,d$ in a proximal direction. The result is that the proximal ends 36 of the blades 32 $a,b,c,d$ are forced out of their respective distal notches 44 and into their respective intermediate notches 46. Due to the increased radial distance of the intermediate notches 46 relative to the radial distances of the distal notches 44, the blades 32 $a,b,c,d$ are spread outwardly and cutter 10 assumes its expanded configuration as shown in FIG. 4B. In this expanded configuration, the cutter 10 is rotated to cut plaque 24 from the stenosis in artery 22.

For removal of the cutter 10 from the artery, cutter 10 must again be placed in its compressed configuration for withdrawal through the introducer catheter 26. This is accomplished by again pulling proximally on guide wire 14 to urge abutment 28 into contact with grommet 38. As can be appreciated by cross referencing FIGS. 4B and 4C, this time the proximal ends 36 of the blades 32 $a,b,c,d$ are forced from the intermediate notches 46 and into the proximal notches 48. Accordingly, cutter 10 is placed into its compressed configuration for retrieval from artery 22 through introducer catheter 26. It is also seen in FIG. 4C that each groove 40 on hub 30 ends with a stop 52 which prevent any further proximal movement of the blades 32 $a,b,c,d$ on hub 30 after they have been engaged with the proximal notches 48.

Figure 5:
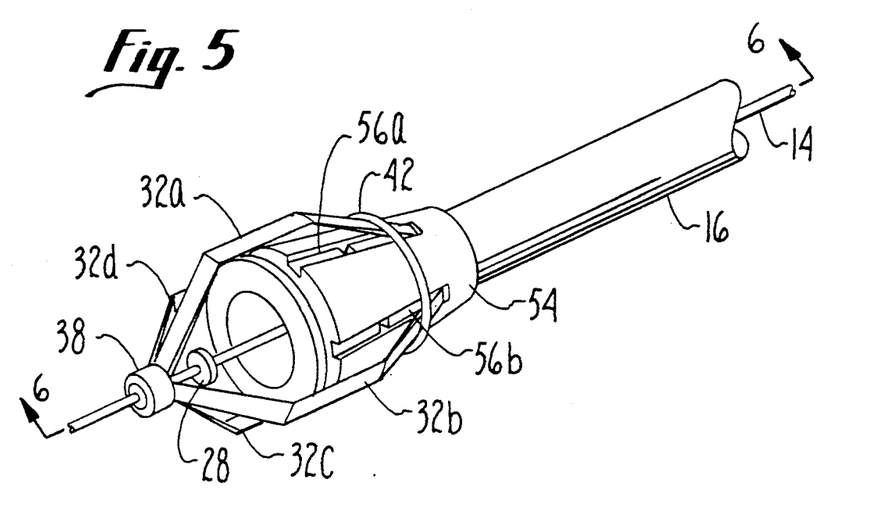
FIG. 5 is a perspective view of an alternate embodiment of the expandable/compressible cutter of the present invention.

In an alternate embodiment of the present invention shown in FIG. 5 two structural differences are apparent. First, the cutter 10 includes a hub 54 which is different from the hub 30 shown for the embodiment in FIG. 3. Second, the abutment 28 is located proximally, rather than distally, from the grommet 38. These structural differences create some change in the operational manipulation of the cutter 10.

As shown in FIG. 5 the hub 54 includes a plurality of grooves 56 $a,b$ (corresponding grooves 56 $c,d$ not shown) and as for the preferred embodiment, the grooves 56 are formed with notches. Specifically, each groove 56 is formed with a proximal notch 58, an intermediate notch 60 and a distal notch 62. Using an axis of rotation defined similarly to that for the preferred embodiment, each proximal notch 58 lies in the same radial plane, and has the same radial distance as each of the other proximal notches 58. Likewise each intermediate notch 60 and each distal notch 62 are established in respective similar radial planes and with respective equal radial distances. Further, each groove 56 has opposed sides 64 which, as for the preferred embodiment, contain the blades 32 $a,b,c,d$ in their respective groove 56 during rotation of the hub 54 by the rotatable torque tube 16.

Figure 6A:
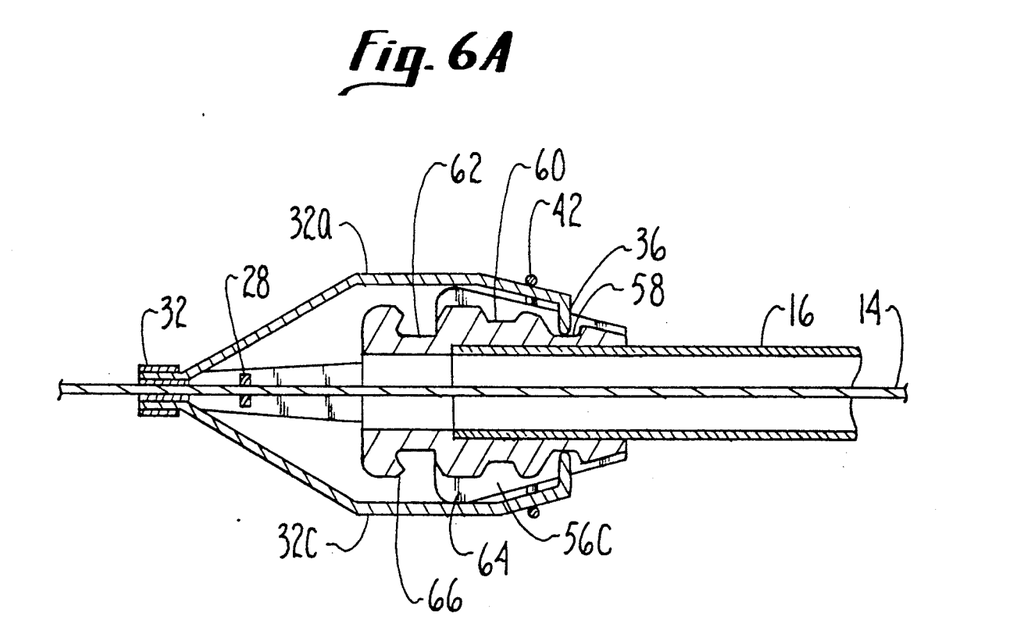
FIG. 6A is a cross-sectional view of the alternate embodiment of the cutter of the present invention in a compressed entry configuration as seen along the line 6—6 in FIG. 5.
Figure 6B:
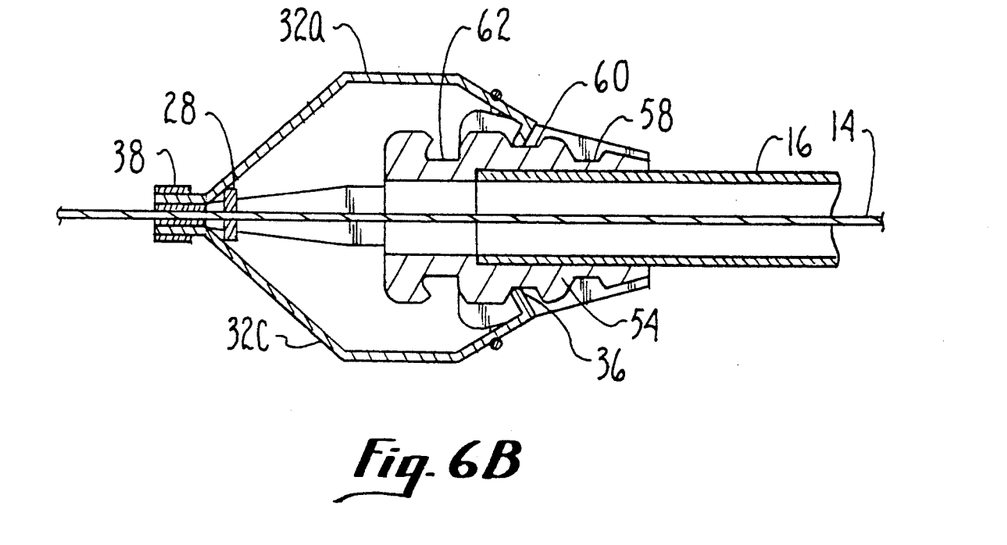
FIG. 6B is a cross-sectional view of the alternate embodiment of the cutter of the present invention as seen in FIG. 6A with the cutter in an expanded configuration.
Figure 6C:
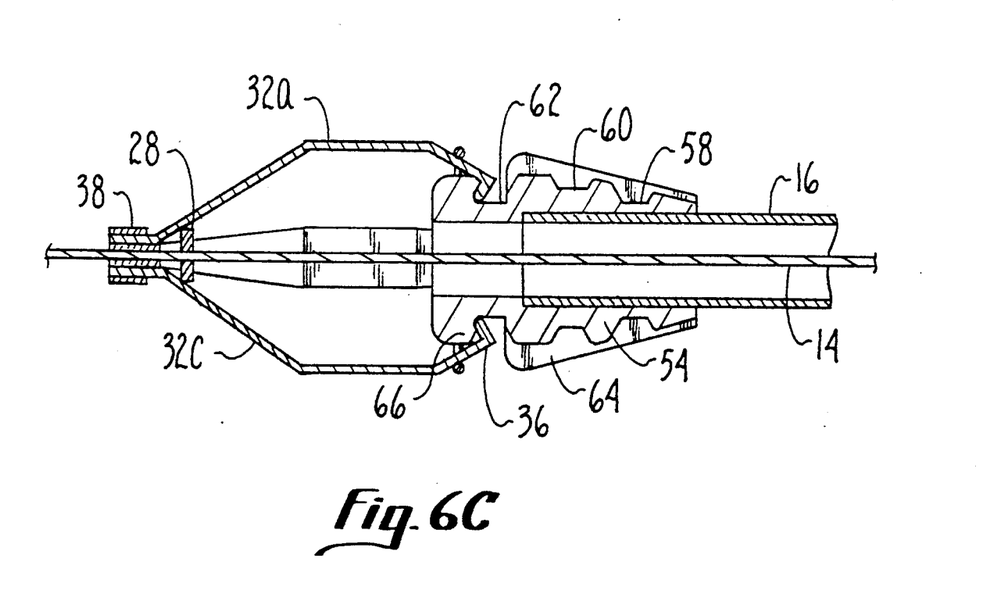
FIG. 6C is a cross-sectional view of the alternate embodiment of the cutter of the present invention as seen in FIG. 6A with the cutter in a compressed withdrawal configuration.

For the operation of the alternate embodiment, cross reference is made between the FIGS. 6A, 6B, and 6C. As shown in FIG. 6A the proximal ends of the blades 32 $a,b,c,d$ are initially located in the proximal notches 58 of hub 56. This places the cutter 10 in its compressed configuration for insertion into the artery 22 through the introducer catheter 26. Manipulation of the cutter 10 from its initial compressed configuration (shown in FIG. 6A) to its expanded configuration (shown in FIG. 6B) is accomplished by pushing distally on the guide wire 14. This causes the abutment 28 to contact the grommet 38 and move the blades 32 a,b,c,d distally relative to the hub 56. Consequently, proximal ends 36 of the blades 32 a,b,c,d are simultaneously moved from proximal notches 58 to the intermediate notches 60 to spread the blades 32 a,b,c,d and place cutter 10 in its expanded position (shown in FIG. 6B). This configuration is used when cutter 10 is rotated to cut plaque 24 from artery 22.

After completion of the atherectomy operation, the cutter 10 is reconfigured into its compressed configuration (shown in FIG. 6C) and withdrawn from the artery 22. To do this, the guide wire 14 is again pushed distally to engaged the abutment 26 with grommet 38. The blades 32 a,b,c,d are then urged further distally relative to the hub 56 and the proximal ends 36 of each blade 32 a,b,c,d is moved from its respective intermediate notch 60 into its respective distal notch 62. A stop 66 is provided on each hub 54 to prevent excessive movement of the blades 32 a,b,c,d in a distal direction.

While the particular compressible/expandable atherectomy cutter as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A compressible/expandable atherectomy cutter which comprises:
   a plurality of cutting blades, each said blade having a distal end and a proximal end;
   a grommet for holding said distal ends of said blades together;
   means engageable with said proximal ends of said blades for moving said blades between a first configuration wherein said blades are compressed to have a reduced cutting radius and a second configuration wherein said blades are expanded to have an increased cutting radius; and
   means for rotating said engageable means with said blades about an axis of rotation.

2. A cutter as recited in claim 1 wherein said rotating means is a torque tube.

3. A compressible/expandable atherectomy cutter which comprises:
   a plurality of cutting blades, each said blade having a distal end and a proximal end;
   means for holding said distal ends of said blades together;
   a hub engageable with said proximal ends of said blades for moving said blades between a first configuration wherein said blades are compressed to have a reduced cutting radius and a second configuration wherein said blades are expanded to have an increased cutting radius, said hub being formed with a plurality of grooves aligned with said axis of rotation, said proximal end of each said blade being slidingly mounted within a separate groove;
   a plurality of axially spaced notches formed in each of said grooves, each said notch lying in a radial plane with a corresponding notch in each of the other of said grooves, said notches in each said radial plane being at the same radial distance from said axis of rotation for simultaneous engagement with said proximal ends of said blades to hold said blades in a selected said configuration; and
   means for rotating said engageable means with said blades about an axis of rotation.

4. A cutter as recited in claim 3 further comprising a spring means positioned around said blades for urging said proximal ends of said blades into said grooves on said hub.

5. A cutter as recited in claim 4 wherein each said groove is formed with at least a distal notch, a proximal notch and an intermediate notch therebetween, said distal notch and said proximal notch having a first radial distance and said intermediate notch having a second radial distance, said first radial distance being less than said second radial distance to respectively establish said first configuration and said second configuration.

6. A cutter as recited in claim 5 wherein said holding means is formed with a hole and said hub is formed with a hole and said cutter further comprises a guide wire insertable through said hole of said holding means and through said hole of said hub, and further, said guide wire being formed with an abutment positioned proximally from said holding means for urging distally against said holding means to move said blades between said first configuration and said second configuration.

7. A cutter as recited in claim 5 wherein said holding means is formed with a hole and said hub is formed with a hole and said cutter further comprises a guide wire insertable through said hole of said holding means and through said hole of said hub, and further, said guide wire being formed with an abutment positioned distally from said holding means for urging proximally against said holding means to move said blades between said first configuration and said second configuration.

8. A cutter as recited in claim 5 wherein said grooves are angled relative to said axis of rotation to facilitate a cyclical movement of said blades from said first configuration, to said second configuration and return to said first configuration.

9. An atherectomy cutter which comprises:
   a rotatable torque tube;
   a hub mounted on said rotatable torque tube for rotation therewith;
   a guide wire formed with an abutment, said guide wire being slidable inserted through said hub and said torque tube;
   a plurality of blades each of said blades having a distal end slidingly engageable with said guide wire and a proximal end engageable with said hub and movable thereon upon urging of said abutment against said distal end to move said blade between a first configuration wherein said blade has a first cutting radius and a second configuration wherein said blade has a second cutting radius, said distal ends of said blades being joined together; and
   means for rotating said hub and said torque tube about an axis of rotation.

10. A cutter as recited in claim 9 wherein said first cutting radius is less than said second cutting radius.

11. A cutter as recited in claim 9 wherein said hub is formed with a plurality of grooves aligned with said axis of rotation, said proximal end of each said blade being slidingly mounted within a separate groove, and each said groove is formed with a plurality of axially spaced notches, each said notch lying in a radial plane with a corresponding notch in each of the other of said grooves, said notches in each said radial plane being at the same radial distance from said axis of rotation for simultaneous engagement with said proximal ends of said blades to hold said blades in a selected said configuration.

12. A cutter as recited in claim 9 wherein each said groove is formed with at least a distal notch, a proximal notch and an intermediate notch therebetween, said distal notch and said proximal notch having a first radial distance and said intermediate notch having a second radial distance, said first radial distance being less than said second radial distance to respectively establish said first configuration and said second configuration.

13. A cutter as recited in claim 9 further comprising a spring means positioned around said blades for urging said proximal ends of said blades into said grooves on said hub.

14. A method for using an atherectomy cutter to excise plaque from the artery of a patient which comprises the steps of:

providing an atherectomy cutter having a rotatable torque tube, a hub mounted on said rotatable torque tube for rotation therewith, a guide wire formed with an abutment, said guide wire being slidable inserted through said hub and said toque tube, and a plurality of blades, each said blade having a distal end slidingly engageable with said guide wire and a proximal end engageable with said hub and movable thereon upon urging said abutment against said distal ends of said blades to move said blades between a first configuration wherein said blades establish a first cutting radius and a second configuration wherein said blades establish a second cutting radius;

configuring said cutter in said first configuration;

inserting said cutter into the artery of a patient and positioning said cutter against the plaque to be excised;

expanding said cutter into said second configuration by positioning the abutment on said guide wire distally from said distal end of said blades and pulling proximally on said guide wire to urge said abutment against said distal ends of said blades to change said configuration thereof; and rotating and advancing said cutter into said artery to excise the plaque.

15. A method as recited in claim 14 wherein said first cutting radius is less than said second cutting radius.

16. A method for using an atherectomy cutter to excise plaque from the artery of a patient which comprises the steps of:

providing an atherectomy cutter having a rotatable torque tube, a hub mounted on said rotatable torque tube for rotation therewith, a guide wire formed with an abutment, said guide wire being slidable inserted through said hub and said toque tube, and a plurality of blades, each said blade having a distal end slidingly engageable with said guide wire and a proximal end engageable with said hub and movable thereon upon urging said abutment against said distal ends of said blades to move said blades between a first configuration wherein said blades establish a first cutting radius and a second configuration wherein said blades establish a second cutting radius;

configuring said cutter in said first configuration;

inserting said cutter into the artery of a patient and positioning said cutter against the plaque to be excised;

expanding said cutter into said second configuration by positioning the abutment on said guide wire distally from said distal end of said blades and pushing distally on said guide wire to urge said abutment against said distal ends of said blades to change said configuration thereof; and rotating and advancing said cutter into said artery to excise the plaque.

* * * * *